(12) United States Patent
Turo et al.

(10) Patent No.: US 8,528,135 B2
(45) Date of Patent: Sep. 10, 2013

(54) SYSTEMS FOR RELIEVING PRESSURE SORES AND METHODS THEREFOR

(76) Inventors: Anthony Michael Turo, Sussex, NJ (US); Kaitlyn Beth Churchman, Sussex, NJ (US); Matthew John Garrera, Branchville, NJ (US); Brandon Andrew Negri, Lafayette, NJ (US)

( * ) Notice: Subject to any disclaimer, the term of this patent is extended or adjusted under 35 U.S.C. 154(b) by 257 days.

(21) Appl. No.: 12/750,833

(22) Filed: Mar. 31, 2010

(65) Prior Publication Data
US 2011/0239370 A1  Oct. 6, 2011

(51) Int. Cl.
*A47B 71/00*  (2006.01)
(52) U.S. Cl.
USPC ........................................ 5/600; 5/613; 5/944
(58) Field of Classification Search
USPC ............. 5/600, 690, 691, 944, 500, 710, 713, 5/714, 715
See application file for complete search history.

(56) References Cited

U.S. PATENT DOCUMENTS

| | | | |
|---|---|---|---|
| 4,982,465 A | | 1/1991 | Nagata et al. |
| 5,549,544 A | * | 8/1996 | Young et al. ...................... 601/2 |
| 5,701,622 A | * | 12/1997 | Biggie et al. ...................... 5/713 |
| 5,926,884 A | * | 7/1999 | Biggie et al. ...................... 5/714 |
| 5,953,773 A | * | 9/1999 | Asada et al. ................. 5/81.1 R |
| 6,015,394 A | * | 1/2000 | Young ............................ 601/55 |
| 6,024,575 A | * | 2/2000 | Ulrich ........................... 434/236 |
| 6,060,804 A | * | 5/2000 | Fujita et al. ...................... 310/81 |
| 6,108,843 A | * | 8/2000 | Suzuki et al. ...................... 5/713 |
| 6,134,970 A | | 10/2000 | Kumakawa et al. |
| 6,165,142 A | | 12/2000 | Bar |
| 6,183,426 B1 | * | 2/2001 | Akisada et al. .................... 601/2 |
| 6,287,253 B1 | | 9/2001 | Ortega et al. |
| 6,721,980 B1 | * | 4/2004 | Price et al. ........................ 5/713 |
| 6,829,797 B2 | * | 12/2004 | Partian .............................. 5/713 |
| 6,953,439 B1 | | 10/2005 | Kabemba |
| 7,330,127 B2 | * | 2/2008 | Price et al. .................... 340/666 |
| 2004/0100376 A1 | | 5/2004 | Lye et al. |
| 2007/0056101 A1 | | 3/2007 | Mahajan et al. |
| 2010/0018327 A1 | * | 1/2010 | Kogure et al. ........... 73/862.041 |

FOREIGN PATENT DOCUMENTS

| | | | |
|---|---|---|---|
| JP | 63279845 A | * | 11/1988 |
| JP | 63300761 A | * | 12/1988 |

* cited by examiner

*Primary Examiner* — Robert G Santos
*Assistant Examiner* — Richard G Davis
(74) *Attorney, Agent, or Firm* — Doherty & Charney LLC

(57) ABSTRACT

A pressure sore relief system includes a plurality of sensors in communication with a surface, whereby each sensor operates independently of one another for detecting a pressure level at a particular region of the surface and generating a feedback signal that corresponds to the detected pressure level, and a system controller adapted to receive the feedback signals from the sensors and generate a plurality of output signals in response to each of the feedback signals. The pressure sore relief system includes a plurality of actuators in communication with the surface and being adapted to receive the output signals from the system controller, whereby each output signal generated by the system controller is associated with one of the actuators. The actuators are adapted to selectively vibrate for minimizing the likelihood of a patient developing pressure sores. The pressure sore relief system may be positioned over a mattress or a chair.

23 Claims, 8 Drawing Sheets

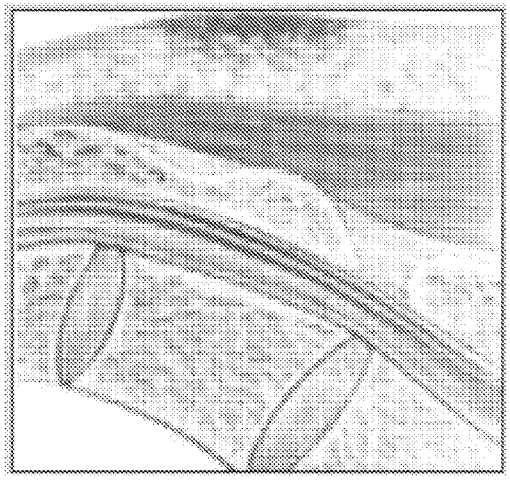
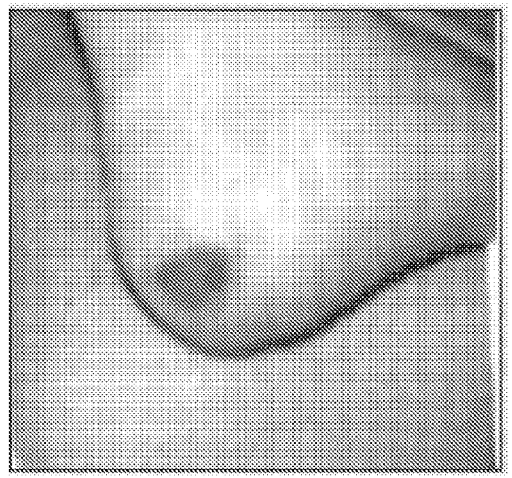
FIG. 2A
Prior Art
FIG. 2B
Prior Art
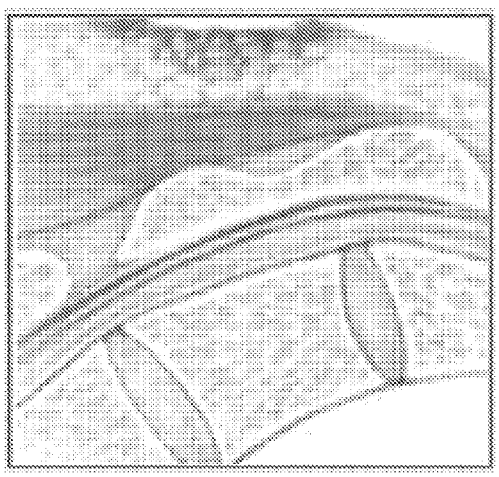
FIG. 3A
Prior Art
FIG. 3B
Prior Art

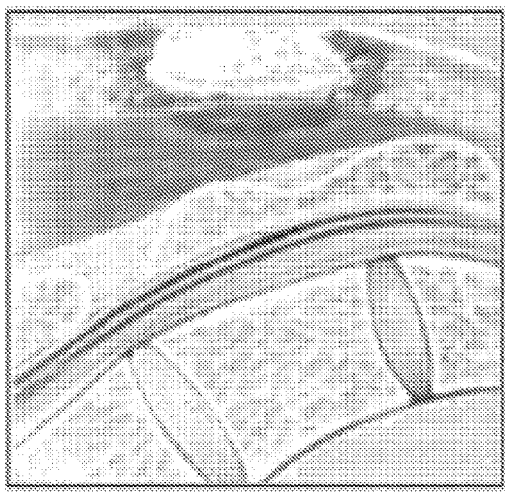
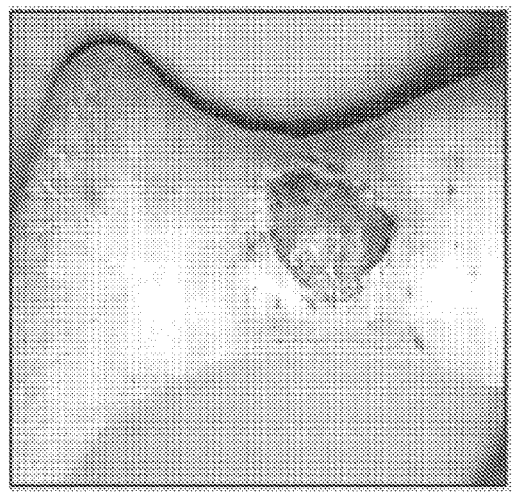
FIG. 4A
Prior Art
FIG. 4B
Prior Art
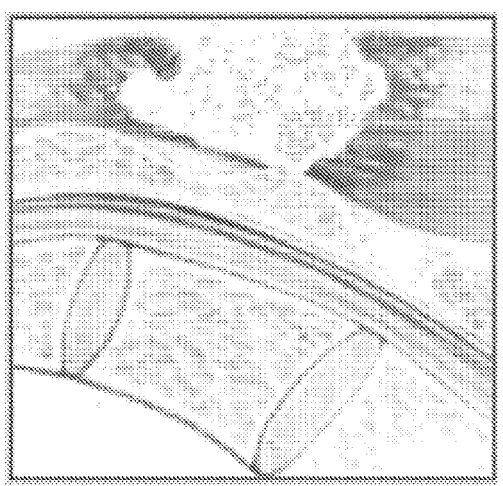
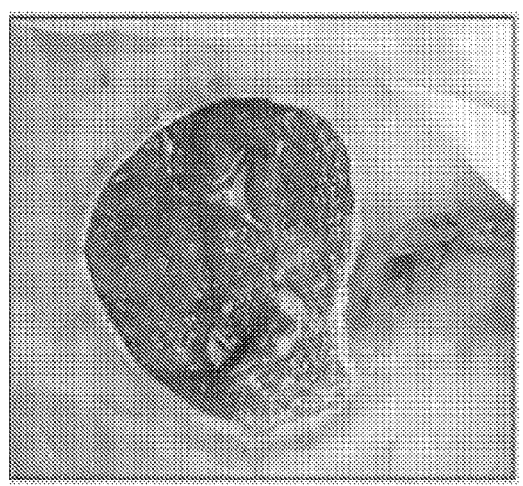
FIG. 5A
Prior Art
FIG. 5B
Prior Art

SYSTEMS FOR RELIEVING PRESSURE SORES AND METHODS THEREFOR

BACKGROUND OF THE INVENTION

1. Field of the Invention

The present invention generally relates to medical devices, and more so specifically relates to medical devices, systems and methods for relieving pressure sores.

2. Description of the Related Art

Pressure sores result when body parts, such as heels, ankles, tailbones, buttocks, or hips, rub against surfaces such as mattresses, bed sheets, and wheel chairs. Pressure sores are not only very painful, but they are also prone to infection, which can spread to the bones and blood stream.

FIGS. 1A-1D show the different points where pressure sores may occur when patients are supported in different positions. The spots on the patient shown in FIGS. 1A-1D indicate where the pressure sores are most likely to occur.

There are four different stages of pressure sores, with stage I being the mildest and stage IV being the worst. Referring to FIGS. 2A and 2B, in stage I, the skin is intact with non-blanchable redness of a localized area usually over a bony protuberance. Darkly pigmented skin may not have visible blanching, however, its color may differ from the surrounding area. Referring to FIGS. 3A and 3B, during stage II, there is a partial thickness loss of the dermis or upper layer of the skin presenting as a shallow open ulcer with a red or pink wound bed, without sloughing. Symptoms may also include an intact or ruptured serum-filled blister.

FIGS. 4A and 4B show stage III whereby there is a full thickness tissue loss. Subcutaneous fat may be visible but bone, tendon and muscle are not exposed. Slough may be present but does not obscure the depth of tissue loss. There may also be undermining and tunneling, whereby the wound infection tunnels under the healthy skin. Referring to FIGS. 5A and 5B, in stage IV there is full thickness tissue loss with exposed bone, tendon and muscle. Slough or eschar may be present on some parts of the wound bed. There may also be undermining and tunneling whereby the wound infection tunnels under the healthy skin.

Those who are most vulnerable to pressure sores are the elderly, stroke victims, patients with diabetes, those with dementia, individuals who use wheelchairs, bedridden patients, and patients with impaired mobility or sensation. Pressure sores typically occur when patients lay on pressure spots such the heels, buttocks, spine, elbows, shoulders and sometimes the head. In some instances, pressure sores may develop in as little as two hours. Pressure sores typically result from prolonged periods of uninterrupted pressure on the skin, soft tissue, muscle and bone.

There are a number of techniques that have been developed for minimizing the likelihood of pressure sores. First, medical personnel can change the position of the patient every two hours, or, if able, the patient can change his or her position. Medical personnel may also check for redness or sores on the skin to help locate pressure sores as early as possible. In addition, medical personnel also maintain the skin as dry as possible. In spite of the above efforts, over a quarter million patients a year suffer pressure sores in stages three and four.

Unfortunately, nurses and medical personnel do not have sufficient time to move patients for minimizing the likelihood of pressure sores. One study found that if medical personnel spent 30-40 minutes a day moving and/or adjusting the position of a patient, the occurrence of pressure sore cases would be reduced by about 300 percent.

In 2007, Medicare data showed that there were over one-quarter of a million cases of pressure sores in the United States. A public health and environment survey for the years 1990-2000 showed that pressure sore cases resulted in approximately 105,7034 deaths. According to one study, the average cost of a hospital stay for treating pressure sores was $43,180.00.

At present, there are a number of systems, devices and methods for minimizing pressure sores. For example, air pressure reducing mattresses, sheepskin, water beds, and sand beds have been used for minimizing pressure sores. U.S. Patent Publication No. 2007/0056101 discloses a system for detecting conditions to prevent a bedsore including a first sensor to detect a first condition that results in the bedsore and to output a first sensor signal from the first sensor indicative of the first condition that results in the bedsore, a controller to receive the first sensor signal and to determine if the condition may result in the bedsore and an alarm responsive to the controller to provide an alarm to indicate that the condition may result in the bedsore. U.S. Pat. No. 6,287,253 discloses a similar type of system for detecting bed sores. In spite of these advances, there remains a need for medical devices, systems and methods that are able to both detect circumstances where pressure sores are likely to occur and that automatically respond for minimizing the likelihood of pressure sores.

SUMMARY OF THE INVENTION

In one embodiment, a pressure sore relief system for a hospital bed preferably includes a plurality of sensors in communication with a surface overlying the hospital bed, whereby each sensor operates independently of one another for detecting a pressure level at a particular region of the surface overlying the bed and generating a feedback signal that corresponds to the detected pressure level. The system desirably has a system controller adapted to receive the feedback signals from the sensors and generate a plurality of output signals in response to each of the feedback signals, and a plurality of actuators in communication with the surface overlying the hospital bed and being adapted to receive the output signals from the system controller, whereby each output signal generated by the system controller is associated with one of the actuators.

In one embodiment, the actuators desirably operate independently of one another and are adapted to generate vibrating forces in response to receiving the output signals. The vibrating forces generated by the actuators have a magnitude, duration, and frequency derived from the output signals. In one embodiment, the magnitude of the vibrating forces increases as the sensed pressure level increases. In one embodiment, the duration of the vibrating forces generated by the actuators is responsive to the pressure levels detected by the sensors. In one embodiment, the frequency of the vibrating forces is responsive to the pressure levels detected by the sensors.

In one embodiment, after a patient is positioned atop a surface, the system controller preferably analyzes data associated with the patient to develop a baseline for the patient. The system controller may be used to establish a threshold pressure value for the patient. In one embodiment, a plurality of pressure threshold values may be established, one for each of the sensors. This information is preferably provided to the controller. The system controller may also preferably include an input device and monitor so that medical personnel may adjust one or more of the pressure threshold values for one or more of the sensors. In one embodiment, medical personnel may lower the pressure threshold value associated with a particular sensor if medical personnel observe a potential problem spot for a pressure sore on a patient's body.

In one embodiment, after the initial set-up for a patient for establishing the pressure threshold values, if any one of the sensors later detects a pressure value that is above the initially-established pressure threshold value, the system controller will desirably generate an output signal that is sent to an actuator associated with the sensor that detected the pressure level that exceeds the threshold value. The system controller preferably activates the actuator for a duration, frequency, and/or magnitude that preferably prevents the development of pressure sores on the patient. In one embodiment, a plurality of sensors may indicate that the pressure threshold values at those respective sensors have been exceeded and the system controller may simultaneously activate the actuators to provide vibrating forces to prevent the development of bed sores.

In one embodiment, the hospital bed includes a mattress, and the surface overlying the hospital bed includes a top surface of the mattress. In one embodiment, the hospital bed includes a mattress and a mattress pad, and the surface overlying the hospital bed is a top surface of the mattress pad. In one embodiment, the mattress pad is preferably adapted to be secured over the mattress.

In one embodiment, at least one of the sensors and at least one of the actuators are combined together into a single element having both sensing and actuating capabilities. The single element may switch back and forth between a sensor phase during which the element senses pressure levels at the surface and an actuator phase during which the element generates vibrating forces at the surface. In one embodiment, the vibrating forces are preferably applied in the region of the surface where the pressure levels were sensed for applying the forces to a patient for preventing the development of bed sores.

In one embodiment, at least one of the sensors may include one or more of the following: piezoelectric elements, strain gauges, laser devices, optical devices, capacitive devices, and/or magnetic devices. In one embodiment, at least one of the actuators may include one or more of the following: piezoelectric elements and motors. In one embodiment, the sensors and the actuators are desirably located within a central region of the surface overlying the hospital bed, whereby the central region of the surface overlying the hospital bed is adapted to support a patient.

In one embodiment, a pressure sore relief system preferably includes a plurality of sensors in communication with a surface adapted to support a patient, whereby each sensor operates independently of one another for detecting a pressure level at a particular region of the surface and generating a feedback signal that corresponds to the detected pressure level. The system desirably includes a system controller adapted to receive the feedback signals from the sensors and generate a plurality of output signals in response to each of the feedback signals, and a plurality of actuators in communication with the surface that are adapted to receive the output signals from the system controller, whereby each output signal generated by the system controller is associated with one of the actuators.

In one embodiment, a pressure sore relief system desirably includes a pad, and a plurality of sensors adjacent a top surface of the pad, whereby each sensor operates independently of one another for detecting a pressure level at a particular region of the top surface of the pad and generating a feedback signal that corresponds to the detected pressure level. The system preferably includes a system controller adapted to receive the feedback signals from the sensors and generate a plurality of output signals in response to each of the feedback signals, and a plurality of actuators adjacent the top surface of the pad and being adapted to receive the output signals from the system controller, whereby each output signal generated by the system controller is associated with one of the actuators. In one embodiment, the system preferably includes a mattress for a bed, whereby the pad includes a mattress pad adapted to be secured over the mattress. In one embodiment, the pad is preferably adapted to be secured over a seat and backrest of a wheelchair.

In one embodiment, a pressure sore relief system for a hospital bed preferably includes a plurality of sensors in communication with a surface overlying the hospital bed, whereby each sensor operates independently of one another for detecting a pressure level at a particular region of the surface overlying the bed and generating a feedback signal that corresponds to the detected pressure level. The system desirably has a system controller adapted to receive the feedback signals from the sensors and generate a plurality of output signals in response to each of the feedback signals, and a plurality of actuators in communication with the surface overlying the hospital bed and being adapted to receive the output signals from the system controller, whereby each output signal generated by the system controller is associated with one of the actuators.

In one embodiment, the actuators desirably operate independently of one another and are adapted to generate vibrating forces in response to receiving the output signals. The vibrating forces generated by the actuators have a magnitude, duration, and frequency derived from the output signals. In one embodiment, the magnitude of the vibrating forces increases as the sensed pressure level increases. In one embodiment, the duration of the vibrating forces generated by the actuators is responsive to the pressure levels detected by the sensors. In one embodiment, the frequency of the vibrating forces is responsive to the pressure levels detected by the sensors.

In one embodiment, the hospital bed includes a mattress, and the surface overlying the hospital bed includes a top surface of the mattress. In one embodiment, the hospital bed includes a mattress and a mattress pad, and the surface overlying the hospital bed is a top surface of the mattress pad. In one embodiment, the mattress pad is preferably adapted to be secured over the mattress.

In one embodiment, at least one of the sensors and at least one of the actuators are combined together into a single element having both sensing and actuating capabilities. The single element may switch back and forth between a sensor phase during which the element senses pressure levels at the surface and an actuator phase during which the element generates vibrating forces at the surface. In one embodiment, the vibrating forces are preferably applied in the region of the surface where the pressure levels were sensed for applying the forces to a patient for preventing the development of bed sores.

In one embodiment, at least one of the sensors may include one or more of the following: piezoelectric elements, strain gauges, laser devices, optical devices, capacitive devices, and/or magnetic devices. In one embodiment, at least one of the actuators may include one or more of the following: piezoelectric elements and motors. In one embodiment, the sensors and the actuators are desirably located within a central region of the surface overlying the hospital bed, whereby the central region of the surface overlying the hospital bed is adapted to support a patient.

In one embodiment, a pressure sore relief system preferably includes a plurality of sensors in communication with a surface adapted to support a patient, whereby each sensor operates independently of one another for detecting a pressure level at a particular region of the surface and generating a feedback signal that corresponds to the detected pressure level. The system desirably includes a system controller adapted to receive the feedback signals from the sensors and generate a plurality of output signals in response to each of the feedback signals, and a plurality of actuators in communication with the surface that are adapted to receive the output signals from the system controller, whereby each output signal generated by the system controller is associated with one of the actuators.

In one embodiment, a pressure sore relief system desirably includes a pad, and a plurality of sensors adjacent a top surface of the pad, whereby each sensor operates independently of one another for detecting a pressure level at a particular region of the top surface of the pad and generating a feedback signal that corresponds to the detected pressure level. The system preferably includes a system controller adapted to receive the feedback signals from the sensors and generate a plurality of output signals in response to each of the feedback signals, and a plurality of actuators adjacent the top surface of the pad and being adapted to receive the output signals from the system controller, whereby each output signal generated by the system controller is associated with one of the actuators. In one embodiment, the system preferably includes a mattress for a bed, whereby the pad includes a mattress pad adapted to be secured over the mattress. In one embodiment, the pad is preferably adapted to be secured over a seat and backrest of a wheelchair.

These and other preferred embodiments of the present invention will be described in more detail below.

BRIEF DESCRIPTION OF THE DRAWING

FIGS. 2A and 2B show a stage I pressure sore.

FIGS. 3A and 3B show a stage II pressure sore.

FIGS. 4A and 4B show a stage III pressure sore.

FIGS. 5A and 5B show a stage IV pressure sore.

DETAILED DESCRIPTION

Figure 1A:
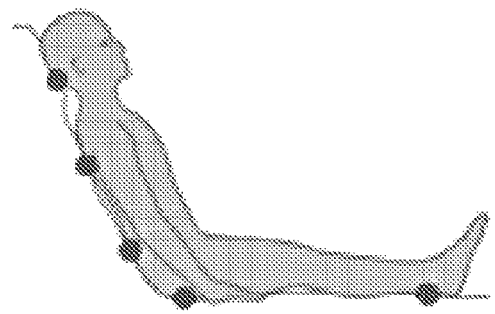
FIG. 1A shows the location of pressure points on a patient when the patient is reclining.
Figure 1B:
FIG. 1B shows the location of pressure points on a patient when the patient is lying on his or her back.
Figure 1C:
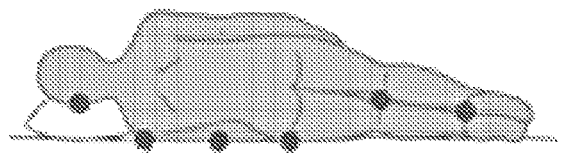
FIG. 1C shows the location of pressure points on a patient when the patient is lying on his or her side.
Figure 1D:
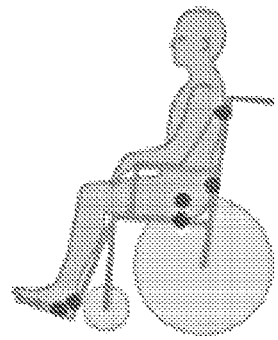
FIG. 1D shows the location of pressure points on a patient when the patient is sitting in a wheelchair.
Figure 6:
FIG. 6 shows a hospital bed including a mattress having a pressure relief system, in accordance with one embodiment of the present invention.

FIG. 6 shows a hospital bed 20 located in a hospital room 22. The hospital bed 20 preferably includes a mattress 24 having a top surface 26. The mattress 24 is adjustable from a substantially flat configuration to the head elevated configuration shown in FIG. 6.

Figure 7A:
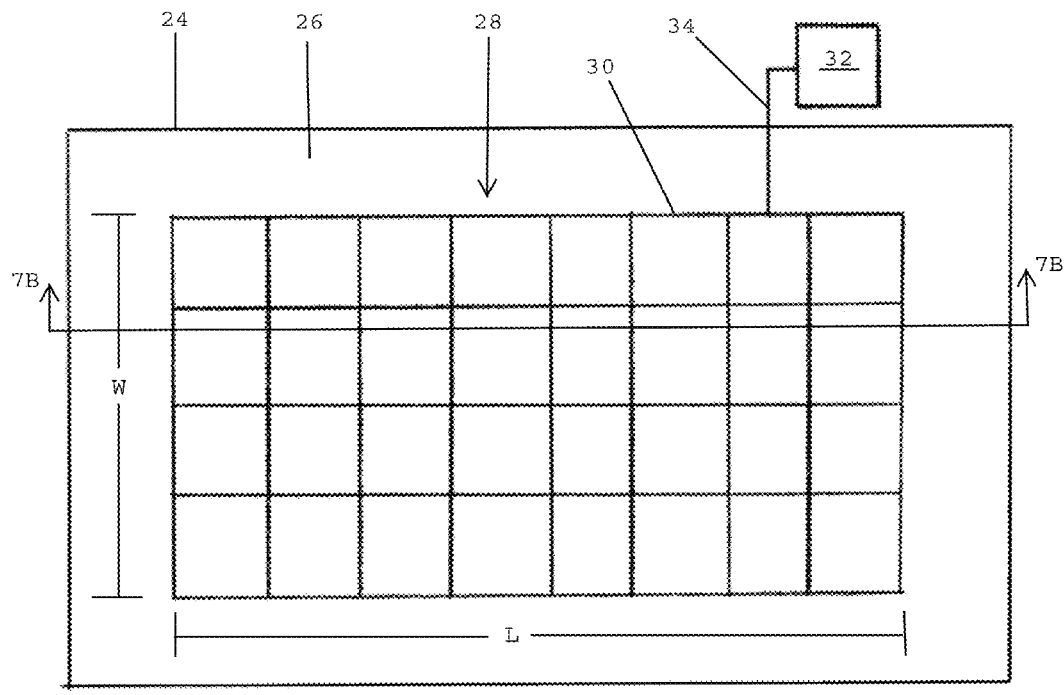
FIG. 7A shows a top plan view of a hospital bed including a mattress having a pressure sore relief system, in accordance with one embodiment of the present invention.

Referring to FIG. 7A, in one embodiment, the top surface 26 of the mattress 24 preferably includes a central area 28 having a length L and a width W. The central area 28 is preferably sized and shaped to accommodate a wide variety of patients having various heights, weights and widths. In one embodiment, the central area 28 of the top surface 26 is sized, shaped and configured to accommodate virtually any patient that may be placed atop the mattress 24.

In one embodiment, the top surface 26 of the mattress 24 is covered by a plurality of sensors/actuators 30 that extend over the central area 28. Each of the sensors/actuators 30 is in communication with a system controller 32 via one or more communication lines 34. In one embodiment, each of the sensors/actuators 30 is preferably adapted to operate independently of the other sensors/actuators.

Figure 7B:
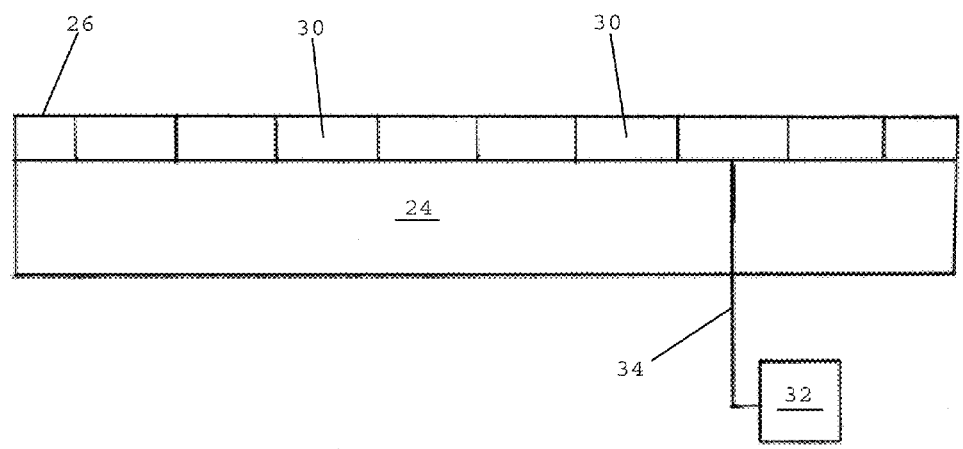
FIG. 7B shows a cross-sectional view of the hospital bed of FIG. 7A taken along line 7B-7B thereof.

Referring to FIG. 7B, in one embodiment, the plurality of sensors/actuators 30 are positioned adjacent the top surface 26 of the mattress 24. In one embodiment, each sensor/actuator is in communication with the top surface 26 of the mattress 24 so that any changes to the top surface may be detected by one or more of the sensors/actuators. For simplicity, only one of the sensors/actuators 30 shown in FIGS. 7A and 7B is coupled with the system controller 32. In preferred embodiments, however, each of the sensors/actuators is coupled with the system controller 32.

Figure 8:
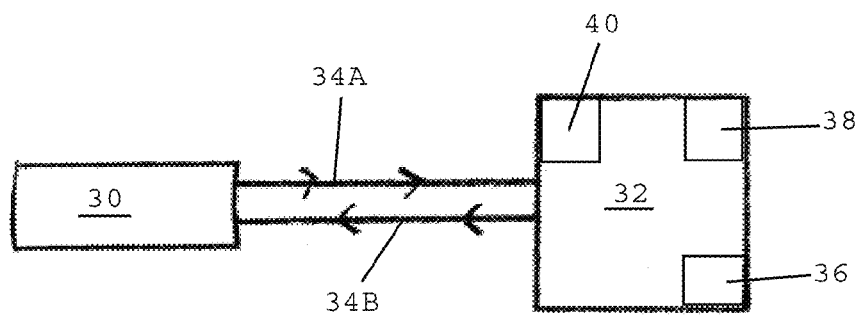
FIG. 8 shows a pressure sore relief system including a combination sensor/actuator and a system controller, in accordance with one embodiment of the present invention.

Referring to FIG. 8, in one embodiment, each of the sensors/actuators 30 is in signal sending and receiving communication with the system controller 32. In one embodiment, each sensor/actuator is adapted to send pressure signals to the system controller via communication line 34A. The system controller 32 preferably analyzes all of the data received from the plurality of sensors/actuators, and sends back one or more control signals to the sensor/actuator 30 via a second communication line 34B. For clarity of illustration, FIG. 8 shows only one sensor/actuator 30, however, it should be understood that all of the sensors/actuators shown in FIGS. 7A and 7B are preferably in signal sending and receiving communication with the system controller 32. In one embodiment, the system controller is adapted to communicate independently with each of the sensors/actuators 30 for receiving independent signals from the sensors and issuing independent controls to the actuators.

In one embodiment, the system controller 32 of the pressure control system may be located anywhere so long as it is in communication with the plurality of sensors/actuators. In one embodiment, the system controller 32 is located within or adjacent the mattress 24. In another embodiment, the system controller may be located in a central location such as a computer center of a hospital. Power for the system controller and one or more pressure sore relief systems may be provided from a stationary power source through a power line.

Referring to FIG. 8, in one embodiment, the system controller 32 preferably includes a microprocessor 36 and a memory device 38 for storing a pressure sore relief strategy or data related to selectively activating one or more of the actuators 30 for treating pressure sore conditions.

In one embodiment, the system controller 32 preferably uses one or more software applications stored therein capable of receiving feedback signals from the sensors, comparing the feedback signals with data stored in the memory device 38, and generating a series of output signals for transmission to the actuators. Upon receiving the output signals, the one or more actuators are actuated for generating vibrations or movement at the top surface 26 of the mattress 24 (FIG. 7B) for treating patients. In one embodiment, the system controller 32 may include an input device 40, such as a computer monitor and keyboard, for inputting patient specific information into the system and/or modifying one or more control programs for the system.

In one embodiment, medical personnel may use the input device 40 for entering data about a particular patient into the system. In one embodiment, medical personnel may input height, weight, and/or age information about a patient so as to maximize system performance for reducing the likelihood of pressure sores. In one embodiment, medical personnel may input information related to a particular area of a body that is likely to suffer from, or that is presently suffering from pressure sores.

In one embodiment, the sensors/actuators 30 are piezoelectric elements that may be used to convert mechanical energy into electrical energy and vice versa. For sensing minor changes in pressure levels and providing high frequency movement in response, the precise sensing and precise motion that results when an electric field is applied to a piezoelectric element is of great value. Sensors and actuators using this effect have changed the world of precision sensing and positioning. As used herein, a piezoelectric sensor or a piezoelectric actuator means a piezoelectric device or element, or any electronic device that operates in a similar fashion to a piezoelectric element such as an electromagnet or a magnetostatic device. In one embodiment, the actuator may be a motor or one or more motors that generate vibration.

In accordance with one embodiment, there is provided a pressure sore relief system that includes a plurality of sensors provided adjacent a top surface of a mattress. The sensors are preferably adapted to detect any changes in pressure applied to the top surface of the mattress so as to generate a plurality of feedback signals proportional to the pressure forces. As used herein, the term "force" includes any force to which the top surface may be subjected to including pressure forces, compressive forces, tensile forces, resonance, vibrations, thermal action, or other process forces. Moreover, the above-identified forces may be applied in any direction with respect to the surface including directions that are substantially perpendicular to the surface and directions that are substantially parallel to the surface.

In one embodiment, the system preferably includes a system controller in communication with each of the sensors for receiving the feedback signals from the sensors and generating output signals responsive to the feedback signals. In one embodiment, the magnitude of the output signal sent to an actuator is preferably proportional to the magnitude of the feedback signal received from the sensor associated with the actuator. In one embodiment, when the sensed pressure increases, the magnitude of the output signal increases so that the actuator generates greater vibration.

The system also preferably includes a plurality of actuators in communication with the surface of the mattress. The actuators may be piezoelectric actuators in signal receiving communication with the system controller for receiving the output signals from the system controller and applying a vibrating force to the surface of the mattress. The vibrating force applied by the piezoelectric actuators adjacent the surface of the mattress are preferably responsive to the input signals received from the sensors.

In one embodiment, applying a plurality of actuators such as piezoelectric actuators adjacent a top surface of a mattress resolves a number of problems associated with existing technologies. Piezoelectric actuators may apply forces independently, and in various combinations, compared to most, if not all, of the existing technologies. Moreover, piezoelectric actuators are extremely precise, allowing for repeatable nanometer and sub-nanometer movements. In addition, piezoelectric actuators may produce significant amounts of force over relatively small areas and are capable of moving heavy loads of up to several hundred pounds. Furthermore, the response time of piezoelectric actuators is in the kilohertz range so that they may be operational at very high frequencies. This is because piezoelectric actuators derive their motion through solid state crystal effects and have no moving parts. In addition, piezoelectric actuators require very little power and require limited or no maintenance.

In one embodiment, the pressure sore relief system includes a plurality of piezoelectric actuators that are provided in communication with or adjacent the top surface of a mattress. In one embodiment, the piezoelectric actuators are piezoelectric foils having a length of approximately 1-5 cm, a width of approximately 1-5 cm, and a height of less than 1 cm. As such, one piezoelectric actuator preferably covers an area of approximately 1-25 $cm^2$. In other preferred embodiments, the piezoelectric actuators may be any size and/or dimension. Thus, the present invention is not limited to using piezoelectric actuators of the size/type listed above. In one embodiment, the present invention preferably includes a plurality of piezoelectric sensors/actuators in communication with the top surface of a mattress so that an infinite combination and array of pressure forces may be sensed and an infinite combination and array of vibrating forces may be applied to the top surface. Because each of the piezoelectric sensors/actuators may be controlled separately by the system controller, it is possible to create virtually any type of vibration pattern or vibration magnitude, thereby providing for unlimited performance possibilities not available in prior art technologies.

In one embodiment, the pressure sore relief system preferably includes a plurality of sensors in communication with the top surface of the mattress. The sensors are preferably adapted for detecting and/or measuring any changes in pressure forces applied to the top surface. In one embodiment, the sensors may be spaced apart from one another and interspersed between the actuators. In one embodiment, the actuators are aligned in rows adjacent or over the top surface of the mattress and the sensors are interspersed between the actuators. The rows of aligned actuators may extend in directions substantially parallel to or perpendicular to the longitudinal axis of a mattress, or may extend in any number of directions between those that are substantially perpendicular and those that are substantially parallel to the longitudinal axis of the mattress. In one embodiment, the ratio of actuators to sensors may be about 100:1. The sensors may be one of a wide variety of sensors including but limited to a piezoelectric element, a strain gauge, a laser used in conjunction with a reflective element, an optical device, a capacitive device and/or a magnetic device. In other preferred embodiments, the ratio of piezoelectric actuators to sensors may vary. In one embodiment, the ratio may be 1:1, or the number of sensors may outnumber the number of actuators. In one embodiment, a sensor and an actuator may be combined into a single, combination sensor/actuator. During a first phase of operation, the combination sensor/actuator may function as a sensor for detecting changes in pressure and for sending detected pressure signals to a system controller. During a later phase of operation, the combination sensor/actuator may transform into an actuator for generating vibration forces. The vibrating forces are preferably proportional to or response to the sensed pressure level. The combination sensor/actuator may change back and forth between phase one operation for sensing and phase two operation for generating vibrating forces.

In one embodiment, the system controller preferably includes a microprocessor and a memory device. The memory may have stored therein look-up tables, a control strategy algorithm and/or an adaptive feedback control strategy algorithm. The system controller is preferably adapted to receive feedback signals from each of the plurality of sensors. The system controller preferably processes the feedback signals to determine whether the signals indicate a sufficient change in pressure at any section of the top surface of the mattress. If an undesirable pressure force is detected at one or more regions of the surface, the controller transmits output signals to the actuators at those particular regions for generating vibrational forces. The magnitude of the vibrational forces may be modified and/or reflective of the magnitude of the pressure changes detected by the sensors.

In one embodiment, the particular form (e.g. frequency) or magnitude of the output signal transmitted to each actuator determines the magnitude, frequency, and/or length of time that a vibrational force is applied to the surface. For example, a sensor may detect only a slight increase in pressure at a particular region of the top surface of the mattress so that the system controller will generate only a slight vibration of the region. On the other hand, if the sensors detect a great increase in pressure, the system controller may provide greater vibrational forces at that region, or vibrational forces that extend for a longer period of time. In one embodiment, the system controller may notify medical personnel when sensed pressure forces are greater than a predetermined threshold value that requires interaction of medical personnel and/or personal inspection of a patient.

Figure 9:
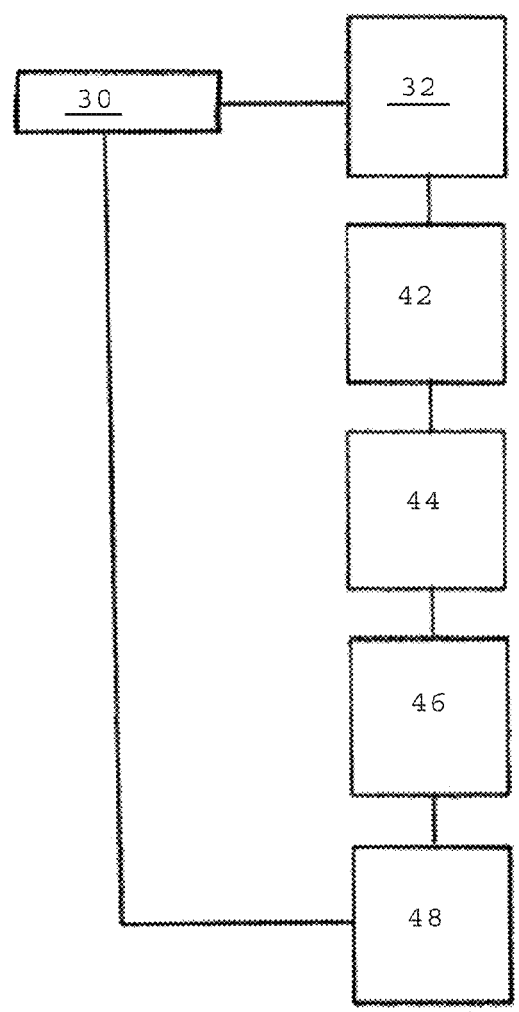
FIG. 9 shows a flow chart for operating a pressure sore relief system including a system controller, in accordance with one embodiment of the present invention.

Referring to FIG. 9, in one embodiment, the system controller is activated so that a sensor/actuator 30 may detect pressure changes, and generate vibrational forces, if necessary. In one embodiment, the sensor/actuator 30 initially functions as a sensor for detecting a change in pressure. The sensor 30 transmits the detected signal to the system controller 32 for analyzing the input signal and determining if any corrective action is required. Although only one sensor 30 is shown in FIG. 9, in one embodiment, a plurality of sensors are sending individual and separate sensing data to the system controller 32 so that the system controller may independently evaluate each of the plurality of inputs. At stage 42, the system controller 32 evaluates all of the inputs and generates possible output signals at stage 44.

At stage 46, the system controller determines one or more output signals to be transmitted to each of the actuators 30. At stage 48 the output signal is sent to the actuator and the actuator generates a vibrational force having a magnitude, frequency, and length determined by the particular commands received from the output signal. Although FIG. 9 shows only one combination sensor/actuator 30, a plurality of sensors/actuators is coupled with the system controller 32. Each of the sensors/actuators operates independently of one another. As a result, a first sensor may detect a pressure change while an adjacent second sensor may make no such reading. As a result, the system controller will preferably generate vibration of the first actuator while the adjacent second actuator remains idle.

Figure 10:
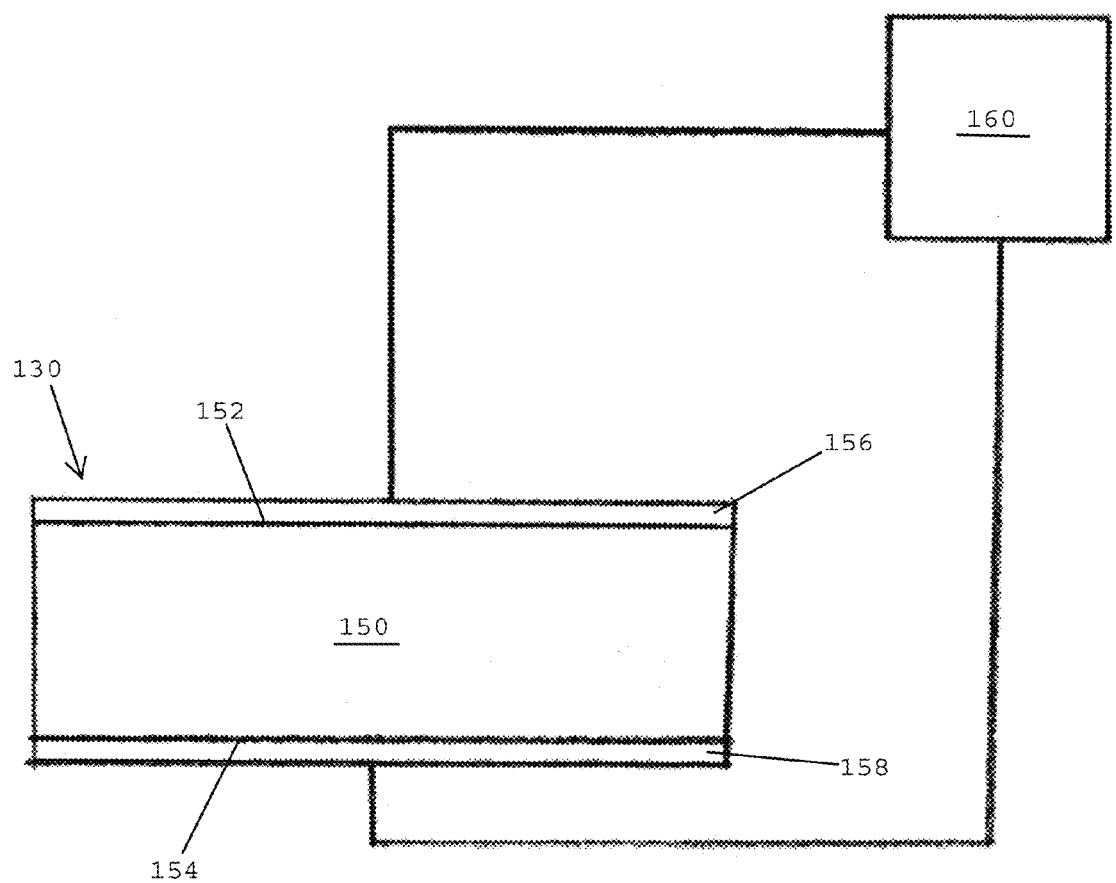
FIG. 10 shows a pressure sensor for a pressure sore relief system, in accordance with one embodiment of the present invention.

Referring to FIG. 10, in one embodiment, a pressure sore relief system includes one or more sensors 130 for detecting changes in a pressure level. In one embodiment, the sensor 130 includes an anti-static foam pad 150 having a top surface 152 and a bottom surface 154. The top surface 152 is desirably covered with a first conductive layer 156 and the bottom surface 154 is preferably covered with a second conductive layer 158. The respective first and second conductive layers 156, 158 are preferably coupled with a comparator 160 that is able to detect any changes in the resistance level through the sensor 130. In one embodiment, when pressure is applied to the sensor 130, the resistance through the sensor drops for indicating a change in pressure. The greater the resistance drops, the greater the pressure increase. In one embodiment, the system controller receives the information from the sensor 130 and generates responsive vibrational forces in that region using any of the vibrational force generating devices disclosed herein.

The headings used herein are for organizational purposes only and are not meant to limit the scope of the description or the claims. As used throughout this application, the word "may" is used in a permissive sense (i.e., meaning having the potential to), rather than the mandatory sense (i.e., meaning must). Similarly, the words "include", "including", and "includes" mean including but not limited to. To facilitate understanding, like reference numerals have been used, where possible, to designate like elements common to the figures.

While the foregoing is directed to embodiments of the present invention, other and further embodiments of the invention may be devised without departing from the basic scope thereof. For example, the present invention contemplates that any of the features shown in any of the embodiments described herein may be incorporated with any of the features shown in any of the other embodiments described herein and still fall within the scope of the present invention.

Figure 11:
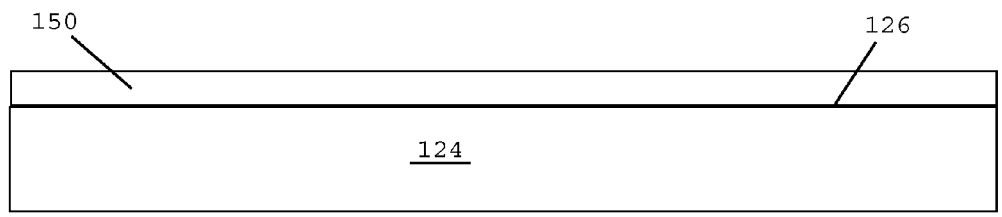
FIG. 11 shows a mattress and a mattress topper overlying the mattress and including a pressure sore relief system, in accordance with one embodiment of the present invention.

Referring to FIG. 11, in one embodiment, a mattress 124 for a bed has a top surface 126. A mattress topper 150 is positioned over the top surface 126 of the mattress 124. The mattress topper 150 preferably includes a pressure sore relief system as described herein. In one embodiment, the mattress topper 150 desirably has pressure sensors and actuators as described herein.

Figure 12:
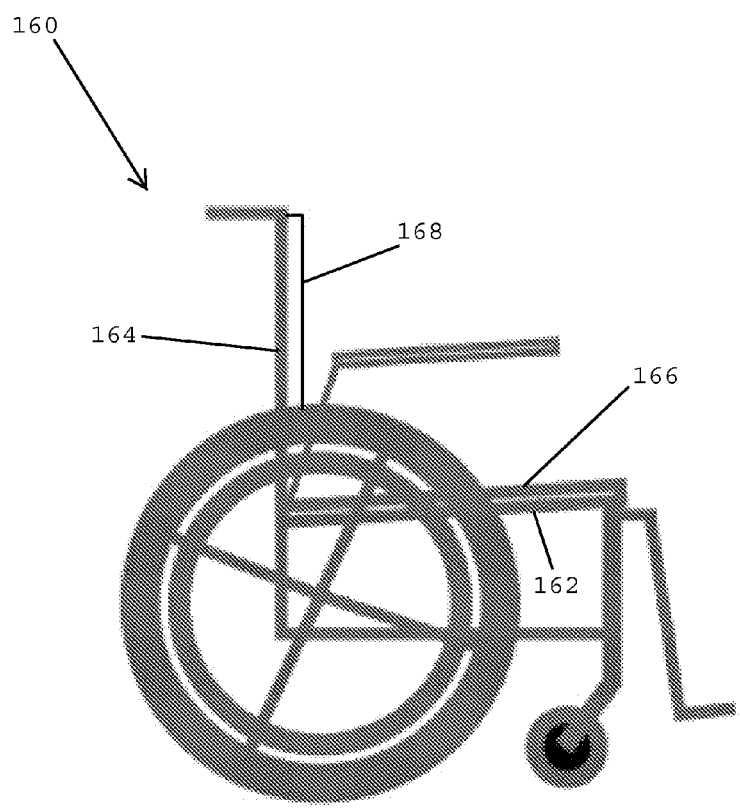
FIG. 12 shows a wheelchair having a seat, a backrest and pads including a pressure sore relief system, in accordance with one embodiment of the present invention.

Referring to FIG. 12, in one embodiment, a wheelchair 160 includes a seat 162 and a backrest 164. A first pad 166 covers the seat 162 and a second pad 168 covers the backrest. In one embodiment, each of the first and second pads 166, 168 desirably includes a pressure sore relief system incorporated therein, as described herein. In one embodiment, only one of the first and second pads may include a pressure sore relief system.

What is claimed is:

1. A pressure sore relief system for a hospital bed comprising:
a plurality of pressure sensors adjacent a top surface of said hospital bed, wherein each said pressure sensor operates independently of one another for detecting changes in pressure forces applied to a particular region of said top surface of said bed and generating a feedback signal that corresponds to said detected changes in pressure forces applied to said top surface of said bed;
a system controller adapted to receive said feedback signals from said pressure sensors and generate a plurality of output signals in response to each of said feedback signals; and
a plurality of actuators in communication with said top surface of said hospital bed and being adapted to receive said output signals from said system controller, wherein each said output signal generated by said system controller is associated with one of said actuators;

wherein said system controller has an initial set-up phase when a patient is positioned atop said top surface of said bed so that a baseline, pressure threshold value is established for each of said pressure sensors for the patient, a first phase of operation during which said system controller receives said feedback signals for detecting whether the baseline, pressure threshold value for the patient has been exceeded for any of said sensors within one or more of regions of said top surface of said bed, and a second phase of operation during which said system controller transmits said output signals to said actuators within the one or more regions for vibrating said top surface of said bed within the one or more regions.

2. The system as claimed in claim 1, wherein said actuators operate independently of one another and are adapted to generate vibrating forces in response to receiving said output signals.

3. The system as claimed in claim 2, wherein said vibrating forces generated by said actuators have a magnitude, duration, and frequency derived from said output signals, and wherein said system controller increases the magnitude of said vibrating forces generated by said actuators as said pressure forces detected by said sensors increase.

4. The system as claimed in claim 1, wherein said hospital bed comprises a mattress, and wherein said surface overlying said hospital bed comprises a top surface of said mattress.

5. The system as claimed in claim 1, wherein said hospital bed comprises a mattress and a mattress pad, and wherein said surface overlying said hospital bed is a top surface of said mattress pad.

6. The system as claimed in claim 5, wherein said mattress pad is adapted to be secured over said mattress.

7. The system as claimed in claim 1, wherein at least one of said sensors and at least one of said actuators are combined together into a single element having both sensing and actuating capabilities.

8. The system as claimed in claim 7, wherein said single element is adapted to switch back and forth between a sensor phase and an actuator phase.

9. The system as claimed in claim 1, wherein at least one of said sensors is selected from the group consisting of piezoelectric elements, strain gauges, laser devices, optical devices, capacitive devices, and magnetic devices.

10. The system as claimed in claim 1, wherein at least one of said actuators is selected from the group consisting of piezoelectric elements and motors.

11. The system as claimed in claim 1, wherein said sensors and said actuators are located within a central region of said surface overlying said hospital bed, and wherein said central region of said surface overlying said hospital bed is adapted to support the patient.

12. A pressure sore relief system comprising:
a plurality of pressure sensors adjacent a surface adapted to support a patient, wherein each said pressure sensor operates independently of one another for detecting changes in pressure forces applied to a particular region of said surface and generating a feedback signal that corresponds to said detected changes in pressure forces applied to said surface;
a system controller adapted to receive said feedback signals from said pressure sensors and generate a plurality of output signals in response to each of said feedback signals; and
a plurality of actuators in communication with said surface and being adapted to receive said output signals from said system controller, wherein each said output signal generated by said system controller is associated with one of said actuators;
wherein said system controller has an initial set-up phase when the patient is positioned atop said surface so that a baseline, pressure threshold value is established for each of said pressure sensors for said patient, a first phase of operation during which said system controller receives said feedback signals for detecting whether the baseline, pressure threshold value for said patient has been exceeded for any of said sensors within one or more regions of said surface, and a second phase of operation during which said system controller transmits said output signals to said actuators within the one or more regions for vibrating said surface within the one or more regions.

13. The system as claimed in claim 12, further comprising a hospital bed, wherein said surface adapted to support said patient overlies said hospital bed.

14. The system as claimed in claim 12, further comprising a wheelchair, wherein said surface adapted to support said patient overlies a seat and a backrest of said wheelchair.

15. The system as claimed in claim 12, wherein at least one of said sensors and at least one of said actuators are combined into a single piezoelectric element in communication with said surface adapted to support said patient.

16. The system as claimed in claim 12, wherein at least one of said sensors is selected from the group consisting of piezoelectric elements, strain gauges, laser devices, optical devices, capacitive devices, and magnetic devices.

17. The system as claimed in claim 12, wherein at least one of said actuators is selected from the group consisting of piezoelectric elements and motors.

18. A pressure sore relief system comprising:
a pad;
a plurality of pressure sensors adjacent a top surface of said pad, wherein each said pressure sensor operates independently of one another for detecting changes in pressure forces applied to a particular region of said top surface of said pad and generating a feedback signal that corresponds to said detected changes in pressure forces;
a system controller adapted to receive said feedback signals from said pressure sensors and generate a plurality of output signals in response to each of said feedback signals; and
a plurality of actuators adjacent said top surface of said pad and being adapted to receive said output signals from said system controller, wherein each said output signal generated by said system controller is associated with one of said actuators;
wherein said system controller has an initial set-up phase when a patient is positioned on said top surface of said pad so that a baseline, pressure threshold value is established for each of said pressure sensors for the patient, a first phase of operation during which said system controller receives said feedback signals for detecting whether the baseline, pressure threshold value for the patient has been exceeded for any of said sensors within one or more regions of said top surface of said pad, and a second phase of operation during which said system controller transmits said output signals to said actuators within the one or more regions for vibrating said top surface of said pad within the one or more regions.

19. The system as claimed in claim 18, further comprising a mattress for a bed, wherein said pad comprises a mattress pad adapted to be secured over said mattress.

20. The system as claimed in claim 18, wherein said pad is adapted to be secured over a seat and backrest of a wheelchair.

21. The system as claimed in claim 1, wherein said actuators comprise an array of actuators including rows extending in a first direction and columns extending in a second direction, and wherein each said row comprises actuators that operate independently of one another and each said column comprises actuators that operate independently of one another.

22. The system as claimed in claim 21, wherein at least one row of said actuators extends between a first side of said bed and a second side of said bed, and wherein at least one column of said actuators extends between a head of said bed and a foot of said bed.

23. The system as claimed in claim 22, wherein said rows of said actuators extend across the width of said bed and said columns of said actuators extend along the length of said bed, and wherein said rows of said actuators cross said columns of said actuators.

\* \* \* \* \*